United States Patent [19]

Cyprien

[11] Patent Number: 4,734,099

[45] Date of Patent: Mar. 29, 1988

[54] ELASTOMERIC SILICONE DEPILATORY

[75] Inventor: Guy Cyprien, L'Hay les Roses, France

[73] Assignee: Rhone-Poulenc Specialties Chimiques, Courbevoie, France

[21] Appl. No.: 836,471

[22] Filed: Mar. 5, 1986

[30] Foreign Application Priority Data

Mar. 5, 1985 [FR] France .................. 85 03178

[51] Int. Cl.$^4$ .................................. A61K 7/155
[52] U.S. Cl. .................................. 8/160; 8/161
[58] Field of Search .................. 8/160, 161

[56] References Cited

U.S. PATENT DOCUMENTS

| | | | |
|---|---|---|---|
| 2,067,909 | 1/1937 | Fetter | 8/160 |
| 2,425,696 | 8/1947 | Herrmann et al. | 8/160 |
| 3,077,465 | 2/1963 | Poruner | 528/32 |
| 3,133,891 | 5/1964 | Ceyzeriat | 528/18 |
| 3,186,963 | 6/1965 | Lewis et al. | 528/18 |
| 3,284,406 | 11/1966 | Nelson | 528/31 |
| 3,409,573 | 11/1968 | Guinet et al. | 528/17 |
| 3,436,366 | 4/1969 | Modic | 524/862 |
| 3,438,930 | 4/1969 | Beers | 524/786 |
| 3,642,685 | 2/1972 | Matherly | 524/785 |
| 3,647,917 | 3/1972 | Schulz et al. | 528/33 |
| 3,678,002 | 7/1972 | Nitzsche et al. | 524/862 |
| 3,697,473 | 10/1972 | Polmanteer et al. | 524/862 |
| 3,862,919 | 1/1975 | Nitzsche et al. | 528/18 |
| 3,886,118 | 5/1975 | Nitzsche et al. | 528/18 |
| 3,888,815 | 6/1975 | Bessmer et al. | 524/703 |
| 3,933,729 | 1/1976 | Letoffè | 524/588 |
| 4,064,096 | 12/1977 | Gibard | 524/847 |
| 4,282,877 | 8/1981 | Mathews | 8/160 |
| 4,340,709 | 7/1982 | Jeram et al. | 528/15 |

FOREIGN PATENT DOCUMENTS

| | | | |
|---|---|---|---|
| 0604711 | 9/1978 | Switzerland | 8/160 |
| 2079762 | 1/1982 | United Kingdom . | |

OTHER PUBLICATIONS

Noll, Walter, *Chemistry and Technology of Silicones*, 2nd edition, pp. 395 to 399, Academic Press (1968).

*Primary Examiner*—Jerome D. Goldberg
*Assistant Examiner*—F. Krosnick
*Attorney, Agent, or Firm*—Burns, Doane, Swecker & Mathis

[57] ABSTRACT

Unwanted hair is removed from selected skin area by applying a coating of a curable organopolysiloxane composition thereon, permitting the organopolysiloxane composition to crosslink into a silicone elastomer, e.g., in the form of a solid layer or foam, and embed unwanted hair therein, and then stripping the silicone elastomer and embedded hair from said skin area, whereby said skin area is essentially depilated.

9 Claims, No Drawings

ELASTOMERIC SILICONE DEPILATORY

BACKGROUND OF THE INVENTION

1. Field of the Invention

The present invention relates to a depilatory composition comprising an organosiloxane material which can be crosslinked at ambient temperature into a silicone elastomer, and to a process for the removal of unwanted hair utilizing such composition.

2. Description of the Prior Art

There are three types of processes known to this art which enable the removal of hair and any hairiness situated on skin areas where its presence is considered to be inappropriate or objectionable, usually for aesthetic reasons.

The first type of process is merely shaving, which has the advantage of being quick and painless, but which has the major disadvantage of not achieving the intended objective. In fact, even immediately after shaving, the hair root, which is flush with the skin, continues to be visible and, furthermore, hairs are strengthened by shaving and grow afresh, stiffer in appearance and longer than prior to shaving.

The second type of process consists of using a cosmetological hair-removing product which is in the form of a liquid or a cream to be spread over the areas to be depilated. The product, which contains calcium or strontium thioglycolate or thiolactate as an active ingredient, dissolves the hair.

To be sure, this process is painless and effective but, since the hair root remains, the hair grows again, sometimes within the skin, requiring frequent successive treatments. In the long run, these numerous treatments can give rise to allergy and/or irritation phenomena.

The third type of process consists of removing the hair, namely, pulling the hairs out with tweezers, a long and tedious process, or, in order to achieve fast hair-removal, by the process of coating the desired area with cold or warm wax, if need be applied with the aid of flexible backings, and again pulling the hairs out, by stripping the wax coating.

This type of process is quick and effective because, since the hair root is pulled out, hair grows again only after several months.

However, in the case where it entails heating of the wax, this process, though having the advantage of being less painful because the warmth softens the hair, has the disadvantage of requiring a costly apparatus, which is difficult to transport. Furthermore, the heat applied to the skin can cause irritation and burns and may even cause varicose veins to appear.

Lastly, the processes such as described in French Pat. No. 2,500,282 and U.S. Pat. No. 4,282,877, which employ wax or a foam made of pressure-adhesive material on a flexible backing, do not enable a satisfactory result to be achieved. In fact, hair removal is generally painful and inadequate, and particles of wax or of an adhesive substance, which are difficult to remove, remain stuck to the skin.

SUMMARY OF THE INVENTION

Accordingly, a major object of the present invention is the provision of improved product/process for cold hair removal, which improved product/process is devoid of those disadvantages and drawbacks to date characterizing the state of this art, or at very least markedly diminishes same.

Another object of this invention is the provision of a hair-removal product which is efficient, economical and easy to use, without any requirement for heating, and completely devoid of toxicity towards the skin.

Briefly, the present invention features a hair-removing product comprising an organopolysiloxane composition which can be crosslinked at ambient temperature into a silicone elastomer.

According to this invention, it has now, quite surprisingly and unexpectedly, been found that the silicone elastomers originating from organopolysiloxane compositions which can be crosslinked at ambient temperature, adhere to hair so strongly that merely pulling a film of elastomer in which the hair is embedded permits the hair to be easily pulled out. This invention, thus, also features a hair-removal process, wherein the area desired to be depilated is covered with a layer of a hair-removing product containing an organopolysiloxane composition which can be crosslinked at ambient temperature into a silicone elastomer in which the hair to be removed is embedded, the layer is permitted to crosslink and the elastomer layer an the hair are removed from the skin by pulling.

DETAILED DESCRIPTION OF THE PREFERRED EMBODIMENTS OF THE INVENTION

More particularly according to the present invention, prior to the hair removal it is preferable to degrease the hair, in order to promote its adhesion within the silicone elastomer. An aqueous solution containing a mild emulsifier with ethyl alcohol can be used for this purpose.

In one embodiment of the invention, a flexible substrate is impregnated or coated, prior to the hair removal, with the depilatory according hereto, and is then applied to the skin. Then, to remove the hair after setting of the silicone, the flexible substrate is quickly pulled away, in jerks.

The organopolysiloxane compositions have the advantage of being completely harmless to the skin.

It is possible to use, within the ambit of the invention, any polysiloxane composition which crosslinks under cold conditions in the presence of atmospheric moisture and/or a crosslinking catalyst and which is presented in a single package (single-component composition) or in two separate packages (two-component composition), the contents of the two packages being mixed extemporaneously at the point in time of use. The depilatory according to the invention is preferably formulated in the form of a liquid or paste.

These organopolysiloxane compositions which can be crosslinked (or can set) when cold, optionally in the form of a foam, are widely known to the silicone art and are described in the literature, especially in the text by Walter Noll, *Chemistry and Technology of Silicones*, 2nd edition, pages 395 to 399, Academic Press (1968).

These organopolysiloxane compositions contain a base organopolysiloxane polymer which ranges from a fluid (at least seven siloxane units per molecule) to a non-flowing gum. As above indicated, any crosslinking system can be used for the siloxane.

It is thus possible to use a wide variety of single-component and two-component compositions which crosslink by means of polyaddition or polycondensation reactions in the presence of a metal catalyst and, if appropriate, an amine and a crosslinking agent, which is typically a silane bearing hydrolyzable functional groups.

The two-component or single-component organopolysiloxane compositions which crosslink at ambient temperature by means of polyaddition reactions, essentially by the reaction of ↑SiH groups borne by a silane or polyorganosiloxane with hydrocarbon groups containing ethylenic, in most cases vinyl, unsaturation, which are bonded to a silicon atom of an organopolysiloxane, typically in the presence of a metal catalyst, preferably platinum, are described, in particular, in U.S. Pat. Nos. 3,220,972, 3,284,406, 3,436,366, 3,697,473 and 4,340,709.

These organopolysiloxane compositions typically contain:

(i) a diorganopolysiloxane polymer containing at least two vinyl radicals bonded to silicon atoms per molecule, and having a viscosity of at least 50 mPa.s at 20° C.;

(ii) a diorganopolysiloxane polymer containing at least 3 hydrogen atoms bonded to silicon atoms per molecule, and having a viscosity of at least 50 mPa.s at 20° C.;

(iv) a catalytically effective amount of a metal or of a metal complex, the metal preferably being platinum, or a platinum group metal.

The two-component compositions which crosslink by polycondensation reactions are the preferred compositions. They typically contain an alpha,omega-dihydroxydiorganopolysiloxane oil, a filler and a crosslinking agent which is a silane containing at least three hydrolyzable groups, or a polysiloxane originating from the partial hydrolysis of this silane, in the presence of a catalytically effective amount of a metal catalyst and/or of an amine; the compositions described in U.S. Pat. Nos. 3,678,002, 3,888,815, 3,933,729, British Pat. No. 2,032,936 and French Pat. No. 1,279,962 are representative.

Particularly preferred from among such elastomeric compositions are those in which the crosslinking agent is a silicate, an alkyltrialkoxysilane or a polysilicate, and in which the metal catalyst is a tin salt, and especially the compositions containing:

(1) at least one alpha,omega-dihydroxydiorganopolysiloxane polymer having a viscosity of 500 to 1,000,000 mPa.s at 25° C., in which the organic radicals are monovalent hydrocarbon radicals, (2) at least one filler, (3) at least one crosslinking agent selected from among the polyalkoxysilanes of the formula:

$$(R_1O)_aSi(R_2)_{4-a} \quad \text{(Ia)}$$

in which a is 3 or 4, $R_1$ and $R_2$, which are identical or different, are each a monovalent hydrocarbon radical containing up to 8 carbon atoms, and $R_1$ can additionally denote a radical $R_3OR_1$, in which $R_3$ is a divalent hydrocarbon radical containing up to 6 carbon atoms and $R_1$ is as defined above; the polyalkoxysiloxanes containing at least two alkoxy radicals bonded to a silicon atom per molecule, in which the silicon atoms are joined via Si—O—Si bonds, the other valencies of the silicon atoms being satisfied by $R_1O$ or $R_2$ radicals, with $R_1$ and $R_2$ being as above defined; and (4) a catalytically effective amount of at least one catalytic tin compound.

The alpha,omega-dihydroxy-diorganopolysiloxane polymers (1) used in the compositions of the invention advantageously have a viscosity of 500 to 1 million mPa.s at 25° C., preferably 800 to 500,000 mPa.s at 25° C.; they are principally comprised of diorganosiloxy units, but the presence of other units such as monoorganosiloxy units in a numerical proportion not exceeding 2% is within the ambit of the invention. Representative organic radicals which are bonded to the silicon atoms in these polymers are those of the following types:

(i) alkyl radicals containing from 1 to 4 carbon atoms, such as methyl, ethyl or propyl radicals;

(ii) haloalkyl radicals containing from 3 to 4 carbon atoms, such as 3,3,3-trifluoropropyl, or 4,4,4-trifluorobutyl radicals;

(iii) aryl radicals containing from 6 to 8 carbon atoms, such as phenyl, tolyl or xylyl radicals;

(iv) haloaryl radicals containing from 6 to 7 carbon atoms, such as chlorophenyl, dichlorophenyl, trichlorophenyl, tetrachlorophenyl or trifluoromethylphenyl radicals; or (v) cyanoalkyl radicals containing from 3 to 4 carbon atoms, such as beta-cyanoethyl or gamma-cyanopropyl radicals.

Methyl radicals constitute at least 60%, preferably of all these organic radicals.

The crosslinking agents (3) employed, as mentioned above, in a proportion of at most 15 parts, preferably at most 7 parts, per 100 parts of polymer (1) principally serve as crosslinking agents for the composition.

The crosslinking agents (3) are well-known materials, described, in particular, in French Pat. Nos. 1,330,625, 2,121,289, 2,121,631 and 2,458,572.

As regards $R_1$ and $R_2$, by "monovalent hydrocarbon radical" there is especially intended alkyl, alkenyl, alkoxyalkyl, phenyl, alkylphenyl and phenylalkyl radicals, optionally substituted by a halogen atom.

Representative, for example, are the silanes of the formulae:
$CH_3Si(OCH_3)_3$
$CH_3Si(OCH_2CH_3)_3$
$CH_3Si(OCH_2CH_2OCH_3)_3$
$Si(OCH_2CH_2OCH_3)_4$
$Si(OCH_3)_4$
$Si(OCH_2CH_3)_4$
$Si(OCH_2CH_2CH_3)_4$
$CH_2=CHSi(OCH_2CH_2OCH_3)_3$
$C_6H_5Si(OCH_3)_3$
$C_6H_5Si(OCH_2CH_2OCH_3)_3$ $$CH_3Si(OCH_2-\underset{\underset{CH_3}{|}}{C}HOCH_3)_3$$

Among the crosslinking agents (3), those especially preferred are alkyltrialkoxysilanes, alkyl silicates and alkyl polysilicates in which the organic radicals are alkyl radicals containing from 1 to 4 carbon atoms.

The alkyl silicates are advantageously selected from among methyl silicate, ethyl silicate, isopropyl silicate, n-propyl silicate, and the polysilicates are advantageously selected from among the products of partial hydrolysis of these silicates; these are polymers comprising a large proportion of units of the formula $(R^4O)_2SiO$ and a small proportion of units of the formula $(R^4O)_3SiO_{0.5}$, $R^4OSi_{1.5}$ and $SiO_2$; the symbol $R^4$ denoting methyl, ethyl, isopropyl or n-propyl radicals. They are usually characterized on the basis of their silica content which is established by analyzing the product of a complete hydrolysis of a specimen.

Methods for preparing the above materials are well known and appear, in particular, in the text *Chemistry and Technology of Silicones*, by W. Noll, on pages 648 to 659. In order to be compatible and/or reactive with the other ingredients used for the preparation of the compositions of the invention, these polymers must be capable of dissolving in the usual hydrocarbon solvents such as toluene, xylene, or methylcyclohexane, in a proportion of at least 50 parts of polymers per 100 parts of solvents.

The polysilicate employed may be, in particular, a partially hydrolyzed ethyl silicate marketed under the trademark "Ethyl Silicate-40" by Union Carbide Corporation, or a partially hydrolyzed propyl silicate.

The compound (4) is a tin catalyst compound used or suggested for catalyzing this type of composition, and which can be, in particular, a tin salt of a mono- or dicarboxylic acid. These tin carboxylates are described, in particular, in the text by Noll [*Chemistry and Technology of Silicones*, page 337, Academic Press, 2nd edition (1968)]. Notably representative are the naphthenate, octanoate, oleate, butyrate, dibutyltin dilaurate and dibutyltin diacetate.

It is also envisaged to use salts of monocarboxylic acids branched on an aliphatic carbon atom in an alpha position relative to the carboxyl group and containing at least 8 carbon atoms per molecule, such as described in French Pat. No. 2,066,159, especially dibutyltin diversatate.

It is also envisaged to use, as a tin catalyst compound, the reaction product of a tin salt, especially of a tin dicarboxylate with ethyl polysilicate, as described in U.S. Pat. No. 3,186,963. The product of reaction of a dialkyldialkoxysilane with a tin carboxylate, as described in U.S. Pat. No. 3,862,919 is also exemplary.

The product of reaction of an alkyl silicate or of an alkyltrialkoxysilane with dibutyltin diacetate, as described in Belgian Pat. No. 842,305, can also be used.

The fillers typically employed in the organopolysiloxane compositions are advantageously a pyrogenic silica, a precipitated silica, diatomaceous earth, calcium carbonate, and ground quartz. For the compositions which crosslink by polycondensation, the silicas are preferably treated with a chlorosilane, a siloxane or a disilazane, such as hexamethyldisilazane, and the organopolysiloxane compositions described in U.S. Pat. Nos. 4,064,096 and 3,642,685, and in French Pat. No. 2,208,937.

The single-component compositions which crosslink by polycondensation reactions with atmospheric moisture, optionally in the presence of a metal catalyst (Ti, Sn), can also be used and typically comprise an alpha,omegadihydroxypolyorganosiloxane oil blocked at each polymer end by at least two hydrolyzable organic groups and a silane bearing at least three hydrolyzable organic groups; the use of this silane is not essential when a blocked oil is employed.

Depending upon the nature of these groups, the single-component compositions are referred to as acidic, neutral or basic.

The compositions described, for example, in U.S. Pat. Nos. 3,035,016, 3,077,465, 3,133,891, 3,409,573, 3,438,930, 3,647,917 and 3,886,118 are representative of the acidic compositions.

The compositions described in U.S. Pat. Nos. 3,065,194, 3,542,901, 3,689,454, 3,779,986 and 4,417,042, British Pat. No. 2,052,540, and European Pat. No. 69,256 are exemplary of the neutral compositions.

The compositions described in U.S. Pat. Nos. 3,378,520, 3,364,260, 3,417,047, 3,464,951, 3,742,004 and 3,758,441 are exemplary of the basic compositions.

The neutral compositions are preferred. It is also possible to use the single-component flowing compositions, such as those described in U.S. Pat. Nos. 3,922,246, 3,965,280 and 4,143,088.

It is also possible to use organosiloxane compositions which crosslink into an elastomer foam.

Compositions of this type, which are more particularly suitable, are described in U.S. Pat. No. 3,070,555.

They contain, preferably:

(1) an alpha,omega-dihydroxydiorganopolysiloxane polymer having a viscosity of at least 50 mPa.s at 25° C.;

(2) a diorganopolysiloxane polymer containing 1 to 75% by weight of siloxane units having a hydrogen atom bonded directly to a silicon atom;

(3) up to 50% by weight, based on the weight of the polymer (1), of at least one compound selected from among silanols, hydroxylated siloxanes of low molecular weight, water and alcohols; and (4) a tin catalyst.

The tin catalyst is preferably stannous octoate.

These compositions can be packaged as an aerosol, as described in European Pat. No. 8034 and in published German Pat. Applications Nos. 2,909,443 and 2,911,971.

They can contain up to 30% by weight of a filler selected from among pyrogenic or precipitated silica, diatomaceous earth, ground quartz, clays and iron oxide.

The organic radicals in the polymers or the silanes (1), (2) and (3) above are similar to those described above for the polymers in the two-component compositions, crosslinking via polycondensation reactions. However, methyl and phenyl radicals are preferred.

In addition, the crosslinking composition in the form of foam may contain a usual filler (silica, diatomaceous earth, ground quartz, etc.).

In order to further illustrate the present invention and the advantages thereof, the following specific examples are given, it being understood that same are intended only as illustrative and in nowise limitative. In said examples to follow, all parts and percentages are by weight.

EXAMPLE 1

The following materials were introduced, in succession, into an 18-liter mixer, fitted with mixing arms with full paddles and maintained under an inert atmosphere by the passage of a slow stream of nitrogen (with the mixing arms rotating):

(i) 3,000 g of a dimethylpolysiloxane oil having a viscosity of 1,000 mPa.s at 25° C., blocked by a group of the formula $(CH_3)_3SiO_{0.5}$ at each end of its polymer chain;

(ii) 1,200 g of a pyrogenic silica having a specific surface of 200 m$^2$/g, containing 1.5% of adsorbed water;

(iii) 96 g of distilled water; and (iv) 240 g of hexamethyldisilazane.

This mixture was stirred at ambient temperature for 6 hours and it was then rid of its volatile components by heating its mass to about 155° C. for 6 hours. A stream of nitrogen passed through the mixer at a flow rate of 200 l/hr throughout the heating period.

To this mixture, cooled to about 80° C., were added, in succession:

(v) 3,000 g of a ground quartz having a mean particle diameter of 5 microns, a specific surface of 15 m$^2$/g, approximately, and containing 1% of adsorbed water;

(vi) 3,000 g of an alpha,omega-dihydroxydimethyl-polysiloxane oil having a viscosity of 16,000 mPa.s at 25° C.; and (vii) 52 g of an alpha,omega-dihydroxydimethyl-polysiloxane oil having a viscosity of 50 mPa.s at 25° C.

The combined materials were mixed for 2 hours; the organopolysiloxane composition formed was then subjected to vigorous grinding by transfer through a hydraulically-clamped 3-roll mill, each roll having a diameter of 120 mm and the clamping pressures being 10 and 20 kg/cm$^2$.

The composition A obtained was stored in the absence of air.

100 g of composition A were mixed with 4.7 g of a setting system B, consisting of:

(a) 3.5 g (as diluent) of a dimethylpolysiloxane having a viscosity of 20 mPa.s at 25° C. and blocked by a group of the formula (CH$_3$)$_3$SiO$_{0.5}$ at each end of its polymer chain;

(b) 0.7 g (as an organosilicon crosslinking agent) of an n-propyl polysilicate, assaying at 34% of silica; and (c) 0.5 g (as a metal catalyst) of dibutyltin dilaurate.

A and B were mixed, by simple stirring.

This composition was spread as a layer approximately 2 mm in thickness onto the calf of a human leg to be depilated, the hair on which having been degreased with an alcohol solution beforehand. After 20 minutes the crosslinked elastomer layer was removed in a single sharp pull and the calf was found to be free of hair.

EXAMPLE 2

The following materials were added, in succession, into the equipment used in Example 1:

(i) 3,000 g of a dimethylpolysiloxane oil having a viscosity of 1,800 mPa.s at 25° C., terminating in a group of the formula (CH$_3$)$_2$CH$_2$=CHSiO$_{0.5}$ at each end of its polymer chain;

(ii) 1,500 g of a pyrogenic silica having a specific surface of 300 m$^2$/g, containing 1.9% of adsorbed water;

(iii) 240 g of distilled water; and (iv) 280 g of the disilazane of the formula (CH$_3$)$_3$SiNHSi(CH$_3$E)$_2$CH=CH$_2$.

The mixture was stirred at ambient temperature for 7 hours, and it was then heated to about 165° C. and maintained at this temperature for 5 hours. During this heating period a stream of nitrogen passed through the mixer at a rate of 250 /hr in order to purge all the volatile products.

To this mixture, cooled to about 70° C., were added, in succession:

(v) 2,500 g of a ground quartz having a mean particle diameter of 7 microns, a specific surface of approximately 10 m$^2$/g and containing 1.3% of adsorbed water;

(vi) 2,800 g of an alpha,omega-dihydroxydimethyl-polysiloxane oil having a viscosity of 25,000 mPa.s at 25° C.; and (vii) 80 g of an alpha,omega-dihydroxydimethyl-polysiloxane oil having a viscosity of 20 cPa.s at 25° C.

The combined materials were mixed for 3 hours at ambient temperature, and the organopolysiloxane composition obtained was then subjected to grinding by transfer through the grinder described in Example 1.

The composition A obtained was stored in the absence of air.

1,000 g of composition A were mixed with 22 g of a setting system B, consisting of:

(a) 12 g (as a diluent) of a dimethylpolysiloxane oil having a viscosity of 20 mPa.s at 25° C., blocked by a group of the formula (CH$_3$)$_3$SiO$_{0.5}$ at each end of its polymer chain;

(b) 4 g (as an organosilicon crosslinking agent) of propyl orthosilicate; and (c) 4 g (as a metal catalyst) of dibutyltin diacetate.

A cotton cloth was impregnated with the mixture of A and B and was applied to the calf of a leg to be depilated. After 25 minutes, after the elastomer had set, the cloth was removed a little at a time and the calf was found to be properly hair-free.

EXAMPLE 3

A first component A was prepared, by mixing:

(i) 630 g of an alpha,omega-dihydroxydimethyl-polysiloxane oil having a viscosity of 3,500 mPa.s at 25° C.;

(ii) 60 g of an alpha,omega-dihydroxydimethyl-polysiloxane oil having a viscosity of 25 mPa.s at 25° C.;

(iii) 60 g of a methylhydropolysiloxane oil blocked by a trimethylsiloxy group at each of its polymer ends, and having a viscosity of 23 mPa.s at 25° C.;

(iv) 30 g of n-propyl orthosilicate;

(v) 60 g of diphenylmethylsilanol; and (vi) 160 g of finely ground quartz.

3 g of stannous octoate were incorporated by mixing into 100 g of component A.

The mixture was spread on the calf of a leg from which hair was to be removed. Foaming took place as soon as the catalyst was incorporated. The foam was in the form of an elastomer within 10–15 minutes and when it was pulled off, the calf which was then uncovered was suitably hair-free.

While this invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the removal of unwanted hair from predetermined skin area, comprising the steps of (a) applying to said skin area an effective depilating amount of a coating of a curable organopolysiloxane composition comprising (i) a diorganopolysiloxane polymer containing at least 2 vinyl radicals bonded to silicon atoms per molecule and having a viscosity of at least 50 mPa.s at 20 C., (ii) a diorganopolysiloxane polymer containing at least 3 hydrogen atoms bonded to silicon atoms per molecule and having a viscosity of at lesat 50 mPa.s at 20 C., (iii) a filler, and (iv) a metal catalyst wherein components (i)–(iv) are present in amounts sufficient to produce a composition which is effective for the removal of hair; (b) permitting said organopolysiloxane composition to crosslink into a silicone elastomer and embed unwanted hair therein; and (c) stripping the silicone elastomer and embedded hair from said skin area, whereby said skin area is essentially depilated.

2. The process as defined by claim 1, said catalyst comprising platinum or a platinum group metal.

3. The process as defined by claim 1, further comprising degreasing said predetermined skin area prior to application of said organopolysiloxane composition thereto.

4. A process for the removal of unwanted hair from predetermined skin area, comprising the steps of (a) applying to said skin area an effective depilating amount of a coating of a curable organopolysiloxane composition comprising (i) an alpha,omega-dihydroxydiorganopolysiloxane oil, (ii) a filler, (iii) a crosslinking agent which comprises a silane containing at least three hydrolyzable groups or a polysiloxane originating from the partial hydrolysis of such silane, and (iv) a metal catalyst, an amine, or mixture thereof wherein components (i)–(iv) are present in amounts sufficient to produce a composition which is effective for the removal of hair; (b) permitting said organopolysiloxane composition to crosslink into a silicone elastomer and embed unwanted hair therein; and (c) stripping the silicone elastomer and embedded hair from said skin area, whereby said skin area is essentially depilated.

5. The process as defined by claim 4, said catalyst comprising a tin salt.

6. The process as defined by claim 4, said filler having been treated with chlorosilane, a siloxane or a disilazane.

7. The process as defined by claim 4, further comprising degreasing said predetermined skin area prior to application of said organopolysiloxane composition thereto.

8. A process for the removal of unwanted hair from predetermined skin area, comprising the steps of (i) applying to said skin area an effective depilating amount of a coating of a curable organopolysiloxane composition comprising (a) an alpha,omega-dihydroxydiorganopolysiloxane polymer having a viscosity of at least 50 mPa.s at 25° C., (b) a diorganopolysiloxane polymer containing from 1 to 75 % by weight of siloxane units containing a hydrogen atom bonded directly to a silicon atom, (c) up to 50% by weight, based on the weight of the polymer (a), of at least one silanol, low molecular weight hydroxylated siloxane, water or alcohol, and (d) tin catalyst wherein components (a)–(d) are present in amounts sufficient to produce a composition which is effective for the removal of hair; (ii) permitting said organopolysiloxane composition to crosslink into an elastomeric silicone foam and embed unwanted hair therein; and (iii) stripping the silicone foam and embedded hair from said skin area, whereby said skin area is essentially depilated.

9. The process as defined by claim 8, further comprising degreasing said predetermined skin area prior to application of said organopolysiloxane composition thereto.

* * * * *